US00PP32916P2

(12) United States Plant Patent
Verduin

(10) Patent No.: US PP32,916 P2
(45) Date of Patent: Mar. 23, 2021

(54) ***ASTILBE* PLANT NAMED 'SUNNY DAY'**

(50) Latin Name: *Astilbe arendsii*
Varietal Denomination: Sunny Day

(71) Applicant: Harrie Verduin, Heemskerk (NL)

(72) Inventor: Harrie Verduin, Heemskerk (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/873,617

(22) Filed: May 21, 2020

(30) Foreign Application Priority Data

Feb. 1, 2020 (QZ) ..... PBR 20200355

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
See application file for complete search history.

*Primary Examiner* — Susan McCormick Ewoldt
(74) *Attorney, Agent, or Firm* — C. A. Whealy

(57) ABSTRACT

A new and distinct cultivar of *Astilbe* plant named 'Sunny Day', characterized by its compact, broadly upright and mounding plant habit; vigorous growth habit; dense and bushy appearance; dark green-colored leaves; freely and uniformly flowering habit; red purple-colored flowers on strong, tall and upright peduncles; and good container and garden performance.

2 Drawing Sheets

Figure 1:
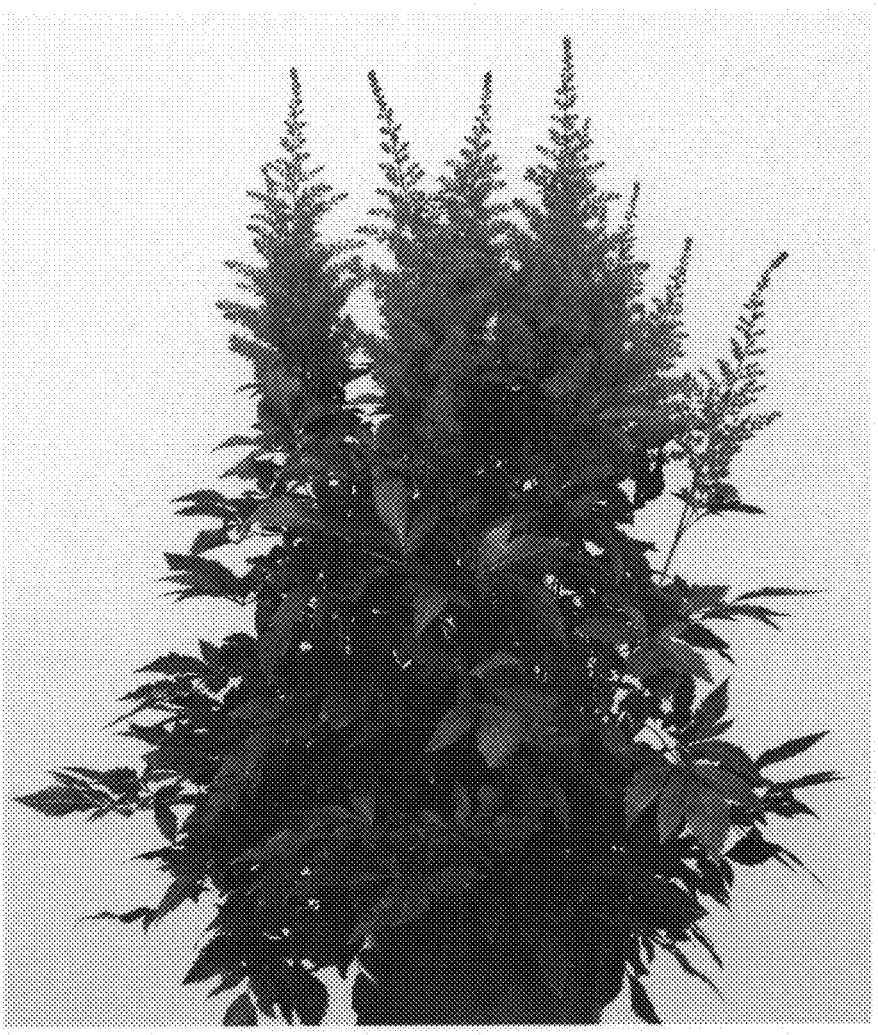

Botanical designation: *Astilbe arendsii.*
Cultivar denomination: 'SUNNY DAY'.

CROSS-REFERENCE TO A RELATED APPLICATION AND STATEMENT REGARDING PRIOR DISCLOSURES BY INVENTOR/APPLICANT

This application claims priority to a European Community Plant Breeders' Rights application filed on Feb. 1, 2020, application number 20200355. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Astilbe*, botanically known as *Astilbe arendsii* and hereinafter referred to by the name 'Sunny Day'.

The new *Astilbe* plant is a product of a planned breeding program conducted by the Inventor in Heemskerk, The Netherlands. The objective of the breeding program was to create new uniform and freely flowering *Astilbe* plants with attractive leaf and flower coloration.

The new *Astilbe* plant originated from a cross-pollination in 2013 in Heemskerk, The Netherlands, of two unidentified

*Astilbe arendsii* seedling selections. The new *Astilbe* plant was discovered and selected by the Inventor as a single flowering plant from within the progeny of the stated cross-pollination in a controlled greenhouse environment in Heemskerk, The Netherlands during the summer of 2015.

Asexual reproduction of the new *Astilbe* plant by vegetative divisions in a controlled nursery environment in Heemskerk, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunny Day'. These characteristics in combination distinguish 'Sunny Day' as a new and distinct *Astilbe* plant:

1. Compact, broadly upright and mounding plant habit.
2. Vigorous growth habit.
3. Dense and bushy appearance.
4. Dark green-colored leaves.
5. Freely and uniformly flowering habit.
6. Red purple-colored flowers on strong, tall and upright peduncles.
7. Good container and garden performance.

Plants of the new *Astilbe* differ primarily from plants of the parent selections in plant habit as plants of the new *Astilbe* are more compact and denser than plants of the parent selections. In addition, inflorescences of plants of the new *Astilbe* are longer than inflorescences of plants of the parent selections.

Plants of the new *Astilbe* can be compared to plants of *Astilbe arendsii* 'Fanal', not patented. In side-by-side comparisons, plants of the new *Astilbe* and 'Fanal' differ primarily in the following characteristics:

1. Plants of the new *Astilbe* are more compact than plants of 'Fanal'.
2. Inflorescences of plants of the new *Astilbe* are smaller than inflorescences of plants of 'Fanal'.
3. Flowers of plants of the new *Astilbe* are red purple in color whereas flowers of plants of 'Fanal' are dark red in color.

Plants of the new *Astilbe* can be compared to plants of *Astilbe arendsii* 'Versred', disclosed in U.S. Plant Pat. No. 23,143. In side-by-side comparisons, plants of the new *Astilbe* and 'Versred' differ primarily in the following characteristics:

1. Plants of the new *Astilbe* are more compact than plants of 'Versred'.
2. Inflorescences of plants of the new *Astilbe* are longer than inflorescences of plants of 'Versred'.
3. Flowers of plants of the new *Astilbe* are brighter red purple in color than flowers of plants of 'Versred'.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1 of 2) is a side perspective view of a typical flowering plant of 'Sunny Day' grown in a container.

Figure 2:
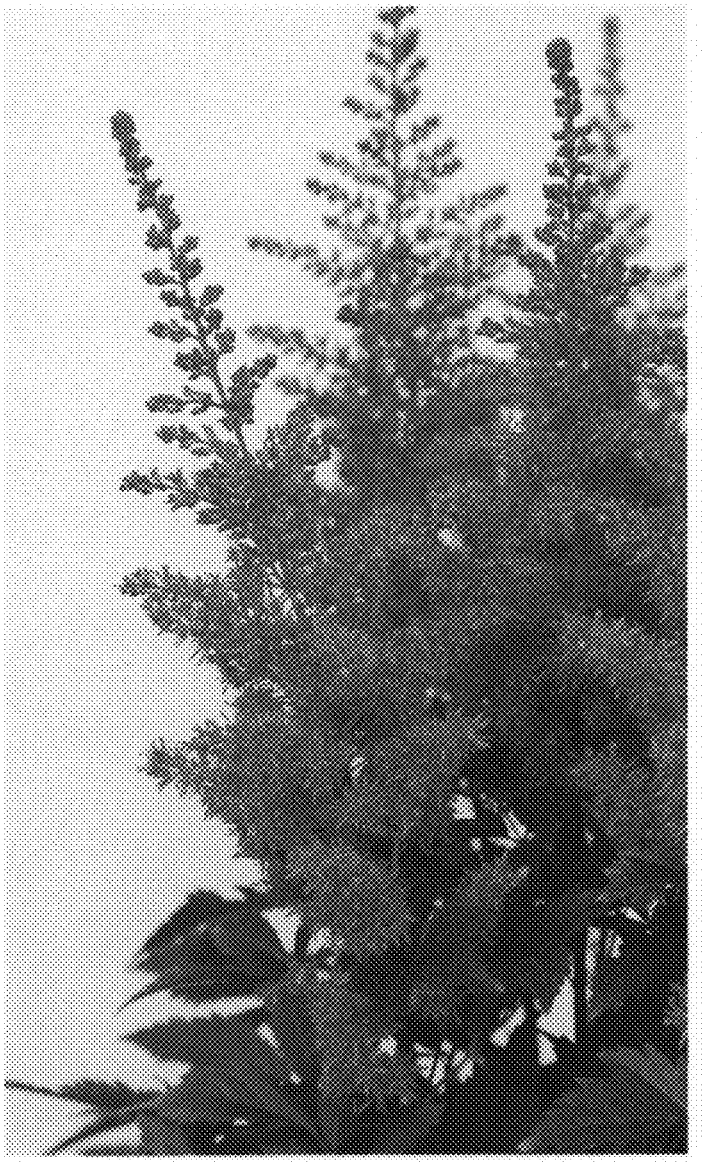

The photograph on the second sheet (FIG. 2 of 2) is a close-up view of typical inflorescences of 'Sunny Day'.

DETAILED BOTANICAL DESCRIPTION

The aforementioned photographs and following observations, measurements and values describe plants grown during the summer in 19-cm containers in an outdoor nursery in Heemskerk, The Netherlands and under cultural practices typical of commercial *Astilbe* production. During the production of the plants, day temperatures ranged from 20° C. to 40° C. and night temperatures ranged from 8° C. to 24° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe arendsii* 'Sunny Day'.

Parentage:

*Female, or seed, parent*.—Unidentified *Astilbe arendsii* seedling selection, not patented.

*Male, or pollen, parent*.—Unidentified *Astilbe arendsii* seedling selection, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; compact, broadly upright and mounding plant form with inflorescences held above the foliar plane; flowering stems and leaves basal; freely flowering with numerous basal branches developing per plant, dense and bushy; vigorous growth habit; and freely and uniformly flowering habit.

*Growth rate*.—Moderately rapid; from divisions, about three months are required to produce fully-grown flowering plants in containers.

*Plant height* (*soil level to top of foliar plane*).—About 36 cm.

*Plant height* (*soil level to top of inflorescences*).—About 54.9 cm.

*Plant width* (*spread*).—About 57 cm.

*Stem description*.—Length: About 27.5 cm. Diameter: About 3 mm. Internode length: About 8.4 cm. Strength: Strong. Aspect: Erect to about 15° from vertical. Texture and luster: Sparsely pubescent; slightly glossy. Color, developing: Close to 143C. Color, developed: Close to 144A.

Leaf description:

*Arrangement*.—Alternate; biternately compound; on average, about 25 leaflets per leaf.

*Leaf length* (*excluding petiole*).—About 17.4 cm.

*Leaf width*.—About 17.3 cm.

*Terminal leaflet length*.—About 7.2 cm.

*Terminal leaflet width*.—About 2.8 cm.

*Lateral leaflet length*.—About 4.6 cm.

*Lateral leaflet width*.—About 1.5 cm.

*Leaf shape, in outline*.—Broadly ovate to broadly deltoid.

*Leaflet shape*.—Elliptic.

*Leaflet apex*.—Acuminate to apiculate.

*Leaflet base*.—Attenuate to narrowly obtuse.

*Leaflet margin*.—Biserrate.

*Leaflet texture and luster, upper and lower surfaces*.—Sparsely pubescent; slightly glossy.

*Leaflet venation pattern*.—Pinnate.

*Leaflet color*.—Developing leaflets, upper surface: Close to 143A. Developing leaflets, lower surface: Close to between NN137A and 147A. Fully expanded leaflets, upper surface: Close to between NN137A and 147A; venation, close to 146D. Fully expanded leaflets, lower surface: Close to between 146A and 147B; venation, close to 153C.

*Leaf petiole length*.—About 17.7 cm.

*Leaf petiole diameter*.—About 2 mm.

*Leaf and leaflet petiole strength*.—Strong.

*Leaf and leaflet petiole texture and luster, upper and lower surfaces*.—Sparsely pubescent; moderately glossy.

*Leaf and leaflet petiole color, upper and lower surfaces*.—Close to 144A; tinged with close to 177D at the base; at the nodes, close to 180A.

Flower description:

*Flower type and flowering habit*.—Single rotate flowers arranged on terminal compound panicles; flowers face upright, outward or downward depending on position on the inflorescence; panicles conical in shape; freely and uniformly flowering habit with about 2,000 flowers developing per inflorescence and about 30,000 flowers developing per plant during the flowering season.

*Fragrance*.—Strong; sweet and pleasant.

*Natural flowering season*.—Plants begin flowering about 13 weeks after planting; continuously flowering from late spring until late summer in The Netherlands.

*Postproduction longevity*.—Flowers last about ten days on the plant; flowers not persistent.

*Flower buds*.—Height: About 3 mm. Diameter: About 2 mm. Shape: Broadly elliptic. Texture and luster: Smooth, glabrous; matte. Color: Sepals, close to 146C and petals, close to 60A.

*Inflorescence height*.—About 24.1 cm.

*Inflorescence diameter*.—About 10.2 cm.

*Flower diameter*.—About 1 cm.

*Flower depth*.—About 4 mm.

*Petals*.—Quantity per flower: Typically five in a single whorl. Length: About 5 mm. Width: About 0.75 mm. Shape: Oblanceolate. Apex: Obtuse. Base: Narrowly cuneate. Margin: Entire; not undulate. Texture and luster, upper and lower surfaces: Smooth, glabrous; matte. Color: Developing petals, upper and lower surfaces: Close to 60C. Fully expanded petals, upper and lower surfaces: Close to 60C; with development, color becoming closer to 60C to 60D.

*Sepals*.—Quantity per flower: Typically five in a single whorl, lower 20% fused towards the base forming a campanulate-shaped calyx. Length: About 1.5 mm. Width: About 1 mm. Shape: Ovate. Apex: Bluntly acute. Base: Cuneate, fused. Margin: Entire. Texture and luster, upper and lower surfaces: Smooth, glabrous; matte. Color: Developing sepals, upper and lower surfaces: Close to 145D; at the margins, close to 59D. Fully expanded sepals, upper and lower surfaces: Close to 157D; at the margins, close to 59D; colors do not change with development.

*Peduncles*.—Length: About 23.7 cm. Diameter: About 2.5 mm. Angle: Mostly erect. Strength: Strong. Texture and luster: Moderately to densely pubescent; slightly glossy. Color: Close to 146C.

*Pedicels*.—Length: About 2 mm. Diameter: About 0.5 mm. Angle: About 40° from peduncle axis. Strength: Moderately strong. Texture and luster: Moderately pubescent; matte. Color: Close to 186B to 186C.

*Reproductive organs*.—Stamens: Quantity per flower: Typically ten; anthers basifixed. Filament length: About 2.5 mm. Filament color: Close to 60B. Anther shape: Broadly ovate. Anther length: About 0.5 mm. Anther diameter: About 0.25 mm. Anther color: Close to 63C. Pollen amount: Scarce. Pollen color: Close to 156D. Pistils: Quantity per flower: Two. Pistil length: About 1.25 mm. Stigma diameter: About 0.1 mm. Stigma shape: Club-shaped. Stigma color: Close to 60C. Style length: About 1 mm. Style color: Close to 60D. Ovary color: Close to 60D.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° to 35° C. and to be suitable for USDA Hardiness Zones 5 through 10.

It is claimed:

1. A new and distinct *Astilbe* plant named 'Sunny Day' as illustrated and described.

* * * * *